United States Patent [19]

Lajoie

[11] Patent Number: 5,422,087
[45] Date of Patent: Jun. 6, 1995

[54] FREE-FLOWING ALKALI METAL BICARBONATE POWDER

[75] Inventor: M. Stephen Lajoie, Basking Ridge, N.J.

[73] Assignee: Church & Dwight Co., Inc., Princeton, N.J.

[21] Appl. No.: 203,266

[22] Filed: Feb. 28, 1994

[51] Int. Cl.$^6$ .......................... C01D 7/00; C01D 7/10
[52] U.S. Cl. ................................. 423/267; 423/275; 423/422
[58] Field of Search ................ 423/265, 267, 275, 422

[56] References Cited

U.S. PATENT DOCUMENTS 5,217,719  6/1993  Yorozu et al. .................. 423/422

Primary Examiner—Wayne Langel
Attorney, Agent, or Firm—Charles B. Barris

[57] ABSTRACT

This invention provides a free-flowing alkali metal bicarbonate composition, which has a content of an acidic inorganic compound such as boron oxide ($B_2O_3$) or phosphorus pentoxide ($P_2O_5$). The acidic inorganic compound reacts with the residual hygroscopic alkali metal carbonate content of the bulk alkali metal bicarbonate powder to form alkali metal bicarbonate.

6 Claims, No Drawings

FREE-FLOWING ALKALI METAL BICARBONATE POWDER

BACKGROUND OF THE INVENTION

Alkali metal bicarbonate is a commodity reagent which has found application in a broad variety of products such as laundry detergents, deodorizers, creams and lotions, dentifrices, antacids, buffers, fungicides, fire extinguishers, and the like.

Alkali metal bicarbonate powder normally does not have a free-flowing capability, which is a disadvantage for purposes of storing and dispensing in bulk quantities.

Commercial scale manufacturing processes produce an alkali metal bicarbonate product which contains a residual quantity of alkali metal carbonate, usually as a trace residue on the surfaces of the crystalline alkali metal bicarbonate particles. Alkali metal carbonate is hygroscopic, and its presence in alkali metal bicarbonate diminishes the free-flow properties of the bulk powder.

Also, when alkali metal bicarbonate is incorporated as a deodorant ingredient in personal care formulations such as cosmetic stick and roll-on antiperspirant products, the presence of an alkali metal carbonate impurity causes skin irritation because of its high pH alkalinity.

There is continuing interest in the availability of bulk alkali metal bicarbonate powder which is free-flowing and substantially free of residual alkali metal carbonate content.

Accordingly, it is an object of this invention to provide an alkali metal bicarbonate powder which is free-flowing and which is essentially free of alkali metal carbonate impurity.

It is another object of this invention to provide a process for reducing the alkali metal carbonate impurity content of bulk alkali metal bicarbonate powder.

Other objects and advantages of the present invention shall become apparent from the accompanying description and examples.

DESCRIPTION OF THE INVENTION

One or more objects of the present invention are accomplished by the provision of a free-flowing powder composition comprising (1) particulate alkali metal bicarbonate and
(2) particulate acidic inorganic compound selected from boron oxides and phosphorus oxides.

The particulate alkali metal bicarbonate powder is selected from sodium bicarbonate, potassium bicarbonate, and mixtures thereof.

The alkali metal bicarbonate powder and the acidic inorganic compound preferably have an average particle size less than about 100 microns.

The content of the acidic inorganic compound in the composition can be in the range between about 0.01–3 weight percent, based on the weight of alkali metal bicarbonate.

Suitable acidic inorganic compounds include boron anhydride ($B_2O_3$), metaboric acid ($HBO_2$), boric acid ($H_3BO_3$), phosphorus trioxide ($P_2O_3$), phosphorus anhydride ($P_2O_5$), and the like.

An invention free-flowing powder composition can contain optional ingredients such as about 0.1–15 weight percent of an anti-caking agent or desiccant, based on the weight of alkali metal bicarbonate.

Illustrative of anti-caking agents are magnesium silicate, calcium silicate, zinc stearate, bentonite, magnesium phosphate, and the like.

Illustrative of desiccants are activated alumina, calcium chloride, silica gel, zinc chloride, and the like. A preferred type of desiccant is a water-deficient inorganic salt such as dehydrated borax ($Na_2B_4O_7.5H_2O$).

In another embodiment this invention provides a process for preparing a free-flowing alkali metal bicarbonate powder which comprises blending particulate alkali metal bicarbonate with between about 0.01–3 weight percent of particulate acidic inorganic compound selected from boron oxides and phosphorus oxides.

Commercial grade alkali metal bicarbonate bulk commodities typically have a content of alkali metal carbonate, which is a residual byproduct of the manufacturing process. Substantially all of the commercial grade alkali metal bicarbonate is produced by carbonation of an aqueous solution of alkali metal carbonate:

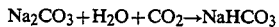

$$Na_2CO_3 + H_2O + CO_2 \rightarrow NaHCO_3$$

A residual quantity (e.g., 0.05–2 weight percent) of alkali metal carbonate is adsorbed as a contaminant on the surfaces of the crystalline alkali metal bicarbonate particles.

The presence of alkali metal carbonate in bulk alkali metal bicarbonate powder is attributable also to an additional factor. Alkali metal bicarbonate decomposes to alkali metal carbonate at elevated temperatures above about 100° C. At ambient temperatures, alkali metal bicarbonate converts to alkali metal carbonate at a constant slow rate.

The presence of a minor quantity of alkali metal carbonate in commercial alkali metal bicarbonate products is acceptable for most applications such as utility as a buffering agent or as the main ingredient in fire extinguisher powders. As noted previously, the presence of alkali metal carbonate in a prospective alkali metal bicarbonate deodorant ingredient is not acceptable in personal care products.

Because of the above considerations, in another embodiment this invention provides a process for reducing a residual alkali metal carbonate content of alkali metal bicarbonate powder which comprises (1) blending the alkali metal bicarbonate powder with particulate acidic inorganic compound selected from boron oxides and phosphorus oxides, wherein the quantity of inorganic compound is up to about 10 acid equivalents per monobasic equivalent of residual alkali metal carbonate; and (2) allowing the alkali metal carbonate and acidic inorganic compound to react in the presence of moisture to form alkali metal bicarbonate.

Typically, the initial residual alkali metal carbonate content is less than about one weight percent of the bulk alkali metal bicarbonate powder.

A reaction occurs between the alkali metal carbonate and acidic inorganic compound over an extended time period under ambient temperature and moisture conditions to form alkali metal bicarbonate:

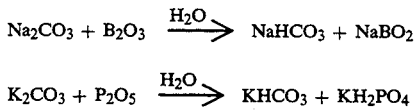

The byproduct borate and phosphate salts are anhydrous when initially formed, and will have desiccant properties.

In accordance with the practice of the present invention embodiments, the alkali metal carbonate content of bulk alkali metal bicarbonate powder can be converted to alkali metal bicarbonate, and the alkali metal bicarbonate can be maintained free of alkali metal carbonate impurity, and be in a free-flowing condition over a long term storage period under ambient conditions.

The following examples are further illustrative of the present invention. The components and specific ingredients are presented as being typical, and various modifications can be derived in view of the foregoing disclosure within the scope of the invention.

EXAMPLE I

This Example illustrates the preparation of a free-flowing sodium bicarbonate powder composition in accordance with the present invention.

A 500 g quantity of commercial sodium bicarbonate (70 micron average particle size; Church & Dwight) is charged to a cone blender, followed by the addition of boron anhydride powder ($B_2O_3$, 5 g). The two particulate ingredients are blended for 10 minutes.

The original sodium bicarbonate powder has a content of 0.6 weight percent of sodium carbonate, and has bulk mobility but is not free-flowing. The quantity of boron anhydride is about 5 acid equivalents per monobasic equivalent of sodium carbonate impurity in the bulk powder.

A sample (100 g) of the blended sodium bicarbonate is transferred to an open erlenmeyer flask, and an equal sample of unblended sodium bicarbonate is placed in a similar flask. The samples are hand-shaken weekly over a period of two months.

The control sample powder becomes less mobile over the test period, and there is evidence of agglomerated particles in the bulk powder. The blended sodium bicarbonate becomes more mobile under the exposure conditions, and has free-flow mobility at the end of the test period.

EXAMPLE II

This Example illustrates the preparation of a free-flowing potassium bicarbonate powder composition in accordance with the present invention.

A 500 quantity of potassium bicarbonate (100 micron average particle size; Church & Dwight) is charged to a cone blender, followed by the addition of phosphorus anhydride powder ($P_2O_5$, 6 g).

The original potassium bicarbonate powder has a content of 1.2 weight percent potassium carbonate, and has bulk mobility but is not free-flowing. The quantity of phosphorus anhydride is about 2 acid equivalents per monobasic equivalent of potassium bicarbonate impurity in the bulk powder.

A sample (100 g) of the blended potassium bicarbonate is transferred to an erlenmeyer flask, and the flask is stoppered. An equal sample of unblended potassium bicarbonate is placed in a similar stoppered flask. The flasks are unstoppered and hand-shaken weekly over a period of three months.

The results are similar to those obtained in Example I. The control powder sample is agglomerated and less mobile, while the blended potassium bicarbonate powder is free-flowing at the end of the test period.

EXAMPLE III

This Example illustrates the preparation of a free-flowing sodium bicarbonate powder composition which contains boric acid and desiccant additives.

A 500 g quantity of commercial sodium bicarbonate (70 micron average particle size; Church & Dwight) is charged to a cone blender, followed by the addition of boric acid ($H_3BO_3$, 7.2 g) and water-deficient borax ($Na_2B_4O_7 \cdot 5H_2O$, 8 g).

The original sodium bicarbonate powder has a content of 1.2 weight percent of sodium carbonate, and has bulk mobility but is not free-flowing. The quantity of boric acid is about 2 acid equivalents per monobasic equivalent of sodium carbonate impurity in the bulk powder.

A sample (100 g) of the blended sodium bicarbonate is transferred to an open erlenmeyer flask. The sample is hand-shaken weekly over a period of five months. At the end of the test period, the test sample powder is free-flowing and without any apparent particle agglomeration.

What is claimed is:

1. A free-flowing powder composition comprising (1) particulate alkali metal bicarbonate which is essentially free of alkali metal carbonate content, and (2) about 0.01–3 weight percent of particulate acidic inorganic compound selected from the group consisting of boron anhydride ($B_2O_3$) and phosphorus anhydride ($P_2O_5$), based on the weight of alkali metal bicarbonate.

2. A powder composition in accordance with claim 1 which contains between about 0.1–15 weight percent of particulate water-deficient borax ($Na2B_4O_7 \cdot 5H_2O$) as a desiccant, based on the weight of alkali metal bicarbonate.

3. A process for reducing a residual alkali metal carbonate content of alkali metal bicarbonate powder which comprises (1) blending the alkali metal bicarbonate powder with particulate acidic inorganic compound selected from the group consisting of boron anhydride ($B_2O_3$) and phosphorus anhydride ($P_2O_5$), wherein the quantity of inorganic compound is up to about 10 acid equivalents per monobasic equivalent of residual alkali metal carbonate; and (2) reacting the alkali metal carbonate and acidic inorganic compound in the presence of moisture to form alkali metal bicarbonate.

4. A process in accordance with claim 3 wherein the initial residual alkali metal carbonate content is less than about one weight percent.

5. A process in accordance with claim 3 wherein the reaction between the alkali metal carbonate and acidic inorganic compound proceeds over an extended time period up to five months under ambient temperature and moisture conditions.

6. A process in accordance with claim 3 wherein the alkali metal bicarbonate powder and the acidic inorganic compound have an average particle size less than about 100 microns.

* * * * *